United States Patent [19]

Levin et al.

[11] Patent Number: 5,281,604
[45] Date of Patent: Jan. 25, 1994

[54] ANGIOTENSIN II RECEPTOR BLOCKING 2,3,6-SUBSTITUTED QUINAZOLINONES

[75] Inventors: Jeremy I. Levin, Nanuet; Aranapakam M. Venkatesan, Elmhurst, both of N.Y.

[73] Assignee: American Cyanamid Company, Wayne, N.J.

[21] Appl. No.: 52,944

[22] Filed: Apr. 23, 1993

[51] Int. Cl.$^5$ .............. C07D 239/91; C07D 403/10; A61K 31/505; A01N 43/54
[52] U.S. Cl. ..................... 514/259; 544/284; 544/287; 514/260
[58] Field of Search ............. 514/259, 260; 544/284, 544/287

[56] References Cited

U.S. PATENT DOCUMENTS

| | | | |
|---|---|---|---|
| 5,202,322 | 4/1993 | Allen et al. | 514/228.2 |
| 5,238,942 | 8/1993 | Chakravarty et al. | 514/259 |
| 5,240,928 | 8/1993 | Allen et al. | 514/259 |

FOREIGN PATENT DOCUMENTS

| | | |
|---|---|---|
| 407342 | 6/1990 | European Pat. Off. . |
| 411766 | 6/1990 | European Pat. Off. . |
| 445811 | 3/1991 | European Pat. Off. . |
| 481448 | 10/1991 | European Pat. Off. . |
| 512870 | 11/1992 | European Pat. Off. . |

*Primary Examiner*—Mukund Shah
*Assistant Examiner*—Matthew V. Grumbling
*Attorney, Agent, or Firm*—Thomas S. Szatkowski

[57] ABSTRACT

The invention provides novel 2,3,6 substituted quinazolinones of the formula

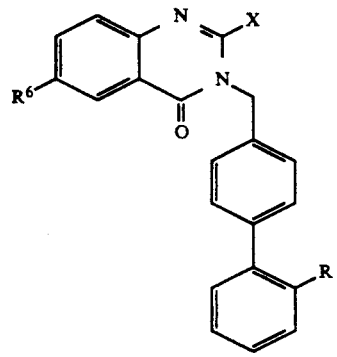

wherein X, R and $R^6$ are defined in the specification which have activity as angiotensin II (AII) antagonists.

21 Claims, No Drawings

ANGIOTENSIN II RECEPTOR BLOCKING 2,3,6-SUBSTITUTED QUINAZOLINONES

BACKGROUND OF THE INVENTION

Field of the Invention

This invention relates to certain novel 2,3, 6 substituted quinazolinone compounds which have demonstrated activity as angiotensin II (AII) antagonists and are therefore useful in alleviating angiotensin induced hypertension and for treating congestive heart failure.

SUMMARY OF THE INVENTION

According to the present invention, there are provided novel compounds of Formula I which have angiotensin II-antagonizing properties and are useful as antihypertensives:

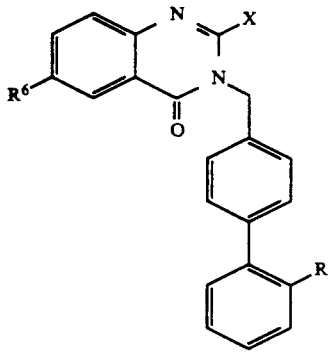

Formula I wherein:
R is

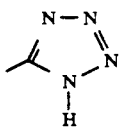

X is straight or branched alkyl of 3 to 5 carbon atoms;
$R^6$ is

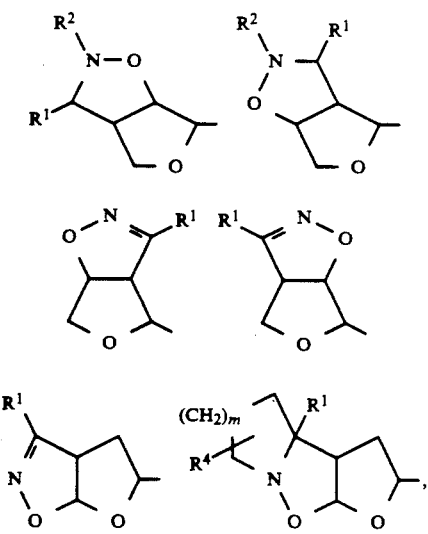

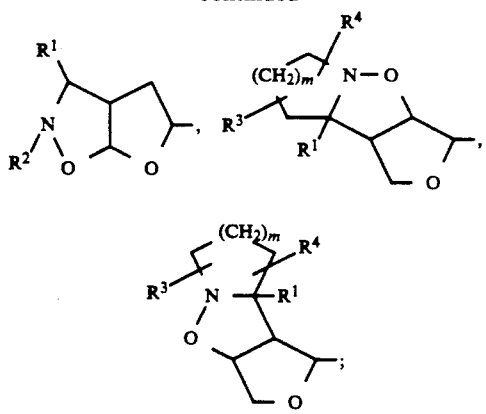

m is 1 or 2

$R^1$ is H, straight chain lower alkyl of 1 to 4 carbon atoms (optionally substituted with $-OR^3$, $-CO_2R^3$, $-CN$, phenyl, substituted phenyl (substitution selected from mono-lower alkyl of 1 to 3 carbon atoms, trifluoromethyl, nitro, O-alkyl of 1 to 3 carbon atoms, F, Cl or Br)), phenyl, substituted phenyl (substitution selected from mono-lower alkyl of 1 to 3 carbon atoms, trifluoromethyl, nitro, O-alkyl of 1 to 3 carbon atoms, F, Cl or Br), $-CN$, $-CO_2R^3$, $-CHO$, $-CON(R^3)_2$, Br, thiophene (optionally substituted with straight chain lower alkyl of 1 to 4 carbon atoms), furan (optionally substituted with straight chain lower alkyl of 1 to 4 carbon atoms);

$R^2$ is H, straight chain lower alkyl of 1 to 4 carbon atoms (optionally substituted with $-OR^3$, $-CO_2R^3$, $-CN$, phenyl, substituted phenyl (substitution selected from mono-lower alkyl of 1 to 3 carbon atoms, trifluoromethyl, nitro, O-alkyl of 1 to 3 carbon atoms, F, Cl or Br)), benzyl, substituted benzyl, (substitution selected from mono-lower alkyl of 1 to 3 carbon atoms, trifluoromethyl, nitro, O-alkyl of 1 to 3 carbon atoms, F, Cl, Br), $-CO_2R^3$, $-SO_2R^{21}$,

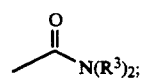

$R^3$ is H, straight chain lower alkyl of 1 to 4 carbon atoms;

$R^4$ is H, straight chain lower alkyl of 1 to 4 carbon atoms;

$R^{21}$ is phenyl, substituted phenyl (substitution selected from mono-lower alkyl of 1 to 3 carbon atoms, trifluoromethyl, nitro, O-alkyl of 1 to 3 carbon atoms, F, Cl or Br)), benzyl, substituted benzyl (substitution selected from mono-lower alkyl of 1 to 3 carbon atoms, trifluoromethyl, nitro, O-alkyl of 1 to 3 carbon atoms, F, Cl, Br) and pharmaceutically acceptable salts of these compounds.

The present invention also provides novel intermediate compounds, methods for making the novel 2, 3, 6 substituted quinazolinone angiotensin II antagonizing compounds, methods for making the novel intermediates, methods of using the novel quinazolinone angiotensin II antagonizing compounds to treat hypertension, congestive heart failure and to antagonize the effects of angiotensin II.

DETAILED DESCRIPTION OF THE INVENTION

The novel compounds of the present invention are prepared according to the following reaction schemes.

Referring to Scheme I, the corresponding anthranilic acid 2 where $R^{10}$ is I, is heated to reflux in alkyl acid anhydride 3 wherein X is alkyl of 3 to 5 carbon atoms to provide the 4H-3,1-benzoxazin-4-ones 4 which are isolated by concentrating the reaction mixtures and used without further purification. When the 4/e,uns/H/ -3,1-benzoxazin-4-ones 4 are refluxed in ethyl alcohol containing ammonia, or ammonium hydroxide solution, the quinazolinone intermediates 5 are obtained.

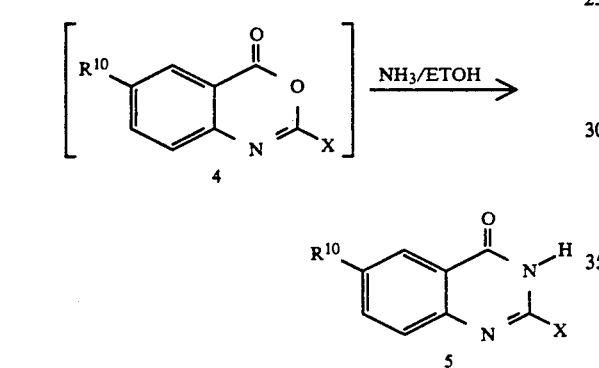

As described in EP 0 497,150, biphenyl 6 is attached to quinazolinone intermediate 5 by initially alkylating the quinazolinone with a para-substituted benzyl bromide and subsequently attaching a second phenyl moiety containing a trityl protected tetrazole or a cyano via a transition metal catalyzed coupling at the para position of the first phenyl ring.

Alternatively, the coupling of quinazolinone intermediate 5, where X is hereinbefore defined, with biphenyl 6 where $R^{18}$ is a trityl protected tetrazole prepared by the method of N. B. Mantlo, *J. Med. Chem.* 34, 2922-2925 (1991), or cyano prepared by the methods outlined in D. J. Carini, *J. Med. Chem.* 34, 2525-2547 (1991) is illustrated in Scheme II and gives coupled product 7 by dissolving 5 and 6 in acetone or another suitable solvent such as N,N-dimethylformamide, N,N-dimethylacetamide, N-methylpyrrolidinone, methanol, ethanol, t-butanol, tetrahydrofuran, dioxane or dimethylsulfoxide, in the presence of excess potassium carbonate or another suitable base such as sodium carbonate, cesium carbonate, sodium hydride, potassium hydride, sodium methoxide, sodium ethoxide, lithium methoxide, lithium ethoxide, sodium t-butoxide, potassium t-butoxide, lithium diisopropylamide (LDA) or lithium hexamethyldisilazide for 2-48 hours, at 20°-60° C. The obtained alkylated quinazolinone 7 may be purified by chromatography or used as is in further transformations.

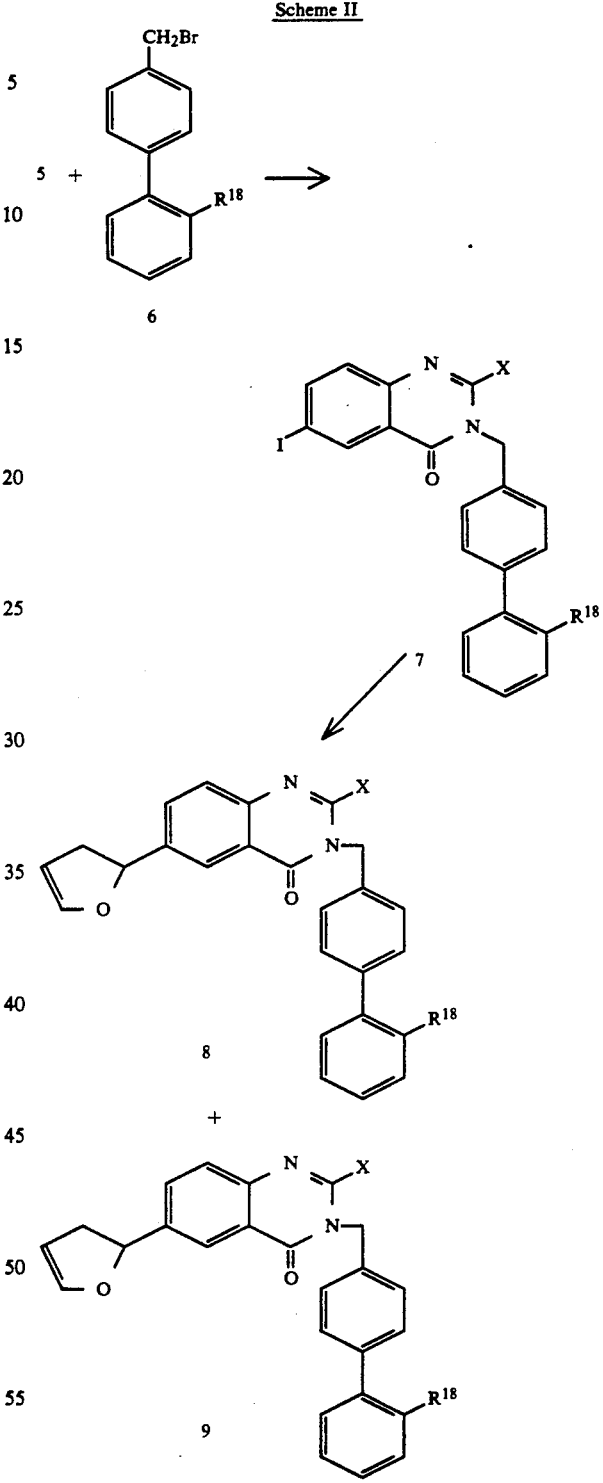

Alkylated quinazolinone 7 is converted to a mixture of the 2,3-dihydro-2-furanyl derivative 8 and the 2,5-dihydro-2-furanyl derivative 9 through a palladium catalyzed coupling with palladium acetate in the presence of 2,3-dihydrofuran. The two compounds are separated by column chromatography on silica gel.

As shown in Scheme III, 10 where $R^1$, $R^3$, $R^4$ and m are hereinbefore defined and $R^{22}$ is OH is reacted with mercuric oxide to give nitrone 11. Alternatively, 10 where $R^1$, $R^3$, $R^4$ and m are hereinbefore defined and $R^{22}$ is H is reacted with selenium dioxide and hydrogen peroxide to also afford nitrone 11.

Scheme III

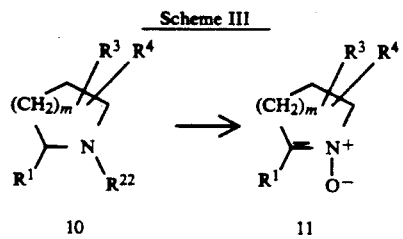

As illustrated in Scheme IV, 9 is reacted with nitrone 11 where $R^1$, $R^3$, $R^4$ and m are hereinbefore defined to give a mixture of 12 and 13 which are separated by column chromatography on silica gel. Additionally, reaction of 8 with nitrone 11 gives 16.

Deprotection of the tetrazole group is accomplished by refluxing an aqueous acetone solution of the alkylated quinazolinone 12, 13 or 16 with a catalytic amount of hydrochloric acid or other suitable acid such as sulfuric, trifluoroacetic or hydrogen chloride for 2-24 hours. Additionally, heating 12, 13 or 16 in tetrahydrofuran-methanol removes the trityl protecting group and affords 14, 15 or 17, respectively. Reaction of 12, 13 or 16 where $R^{18}$ is cyano with sodium azide in the presence of tri-n-butyltin chloride in refluxing xylene affords the desired tetrazole 14, 15 or 17, respectively. Contemplated equivalents to tri-n-butyltin chloride include tri-(lower alkyl $C_1-C_4$) tin chlorides and bromides. Contemplated equivalents to sodium azide include potassium azide, and lithium azide.

Scheme IV

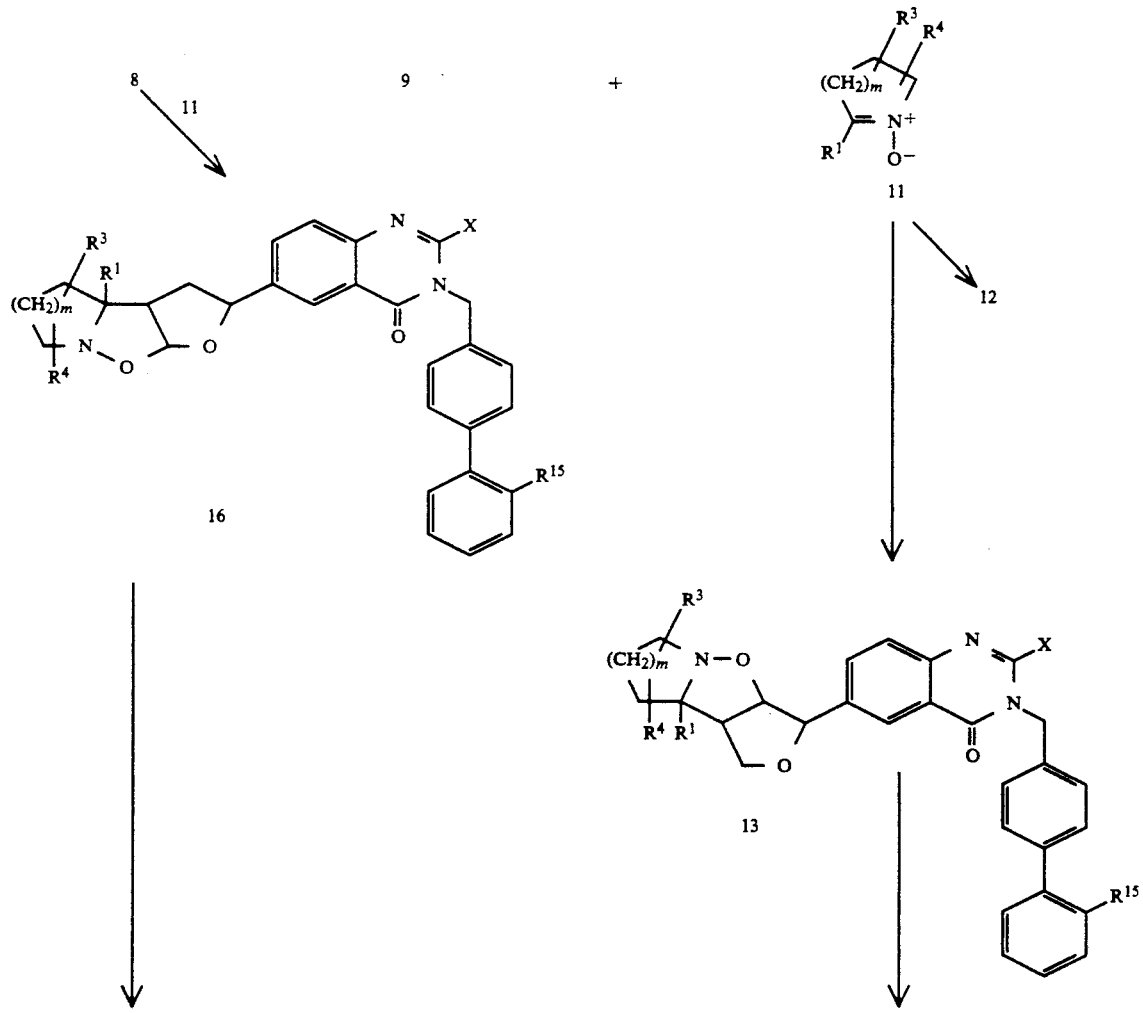

-continued
Scheme IV
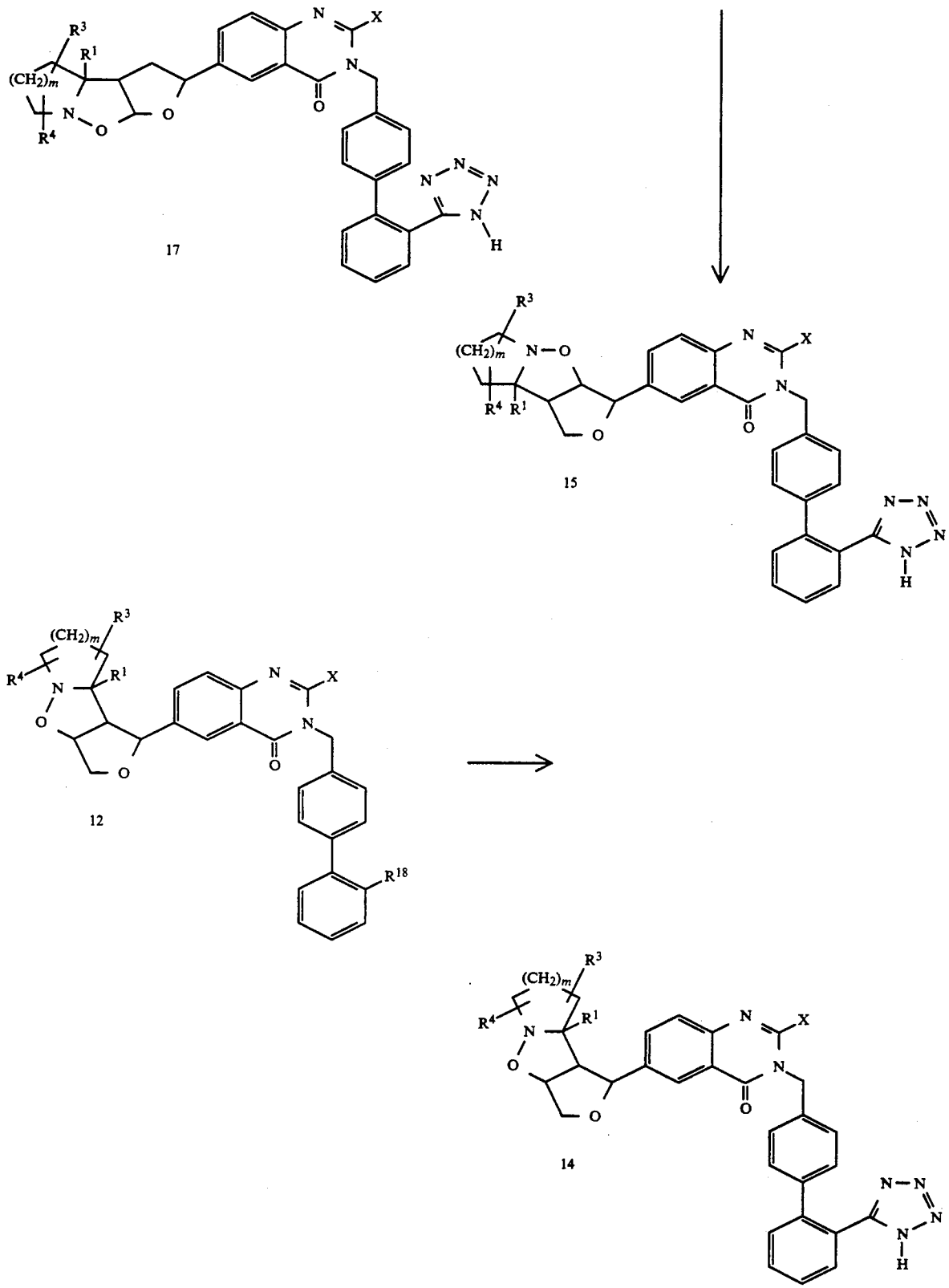
As shown in Scheme V, nitrone 19 where $R^1$ and $R^2$ are hereinbefore defined with the proviso that for this scheme, $R^2$ cannot be $-CO_2R^3$, $-SO_2R^{21}$ or

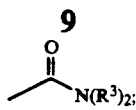

is prepared from 18 by reaction with selenium dioxide and hydrogen peroxide. Nitrone 19 is reacted with 8 to give 20. Nitrone 19 is similarly reacted with 9.

Deprotection of the tetrazole group is accomplished by refluxing an aqueous acetone solution of quinazolinone 20 with a catalytic amount of hydrochloric acid or other suitable acid such as sulfuric, trifluoroacetic or hydrogen chloride for 2–24 hours. Additionally, heating 20 in tetrahydrofuran-methanol removes the trityl protecting group and affords 21. Reaction of 20 where $R^{18}$ is cyano, with sodium azide in the presence of tri-n-butyltin chloride in refluxing xylene affords the desired tetrazole 21. Contemplated equivalents to tri-n-butyltin chloride include tri(lower alkyl $C_1$–$C_4$) tin chlorides and bromides. Contemplated equivalents to sodium azide include potassium azide and lithium azide.

As illustrated in Scheme VI, 8 is reacted with nitrile oxide 22 where $R^1$ is hereinbefore defined to give 25. Nitrile oxide 22 is generated from the corresponding oxime 23 or the corresponding nitro compound 24. Nitrile oxide 22 is similarly reacted with 9.

Deprotection of the tetrazole group is accomplished by refluxing an aqueous acetone solution of quinazolinone 25 with a catalytic amount of hydrochloric acid or other suitable acid such as sulfuric, trifluoroacetic or hydrogen chloride for 2–24 hours. Additionally, heating 25 in tetrahydrofuran-methanol removes the trityl protecting group and affords 26. Reaction of 25 where $R^{18}$ is cyano with sodium azide in the presence of tri-n-butyltin chloride in refluxing xylene afford the desired tetrazole 26. Contemplated equivalents to sodium azide include potassium azide and lithium azide.

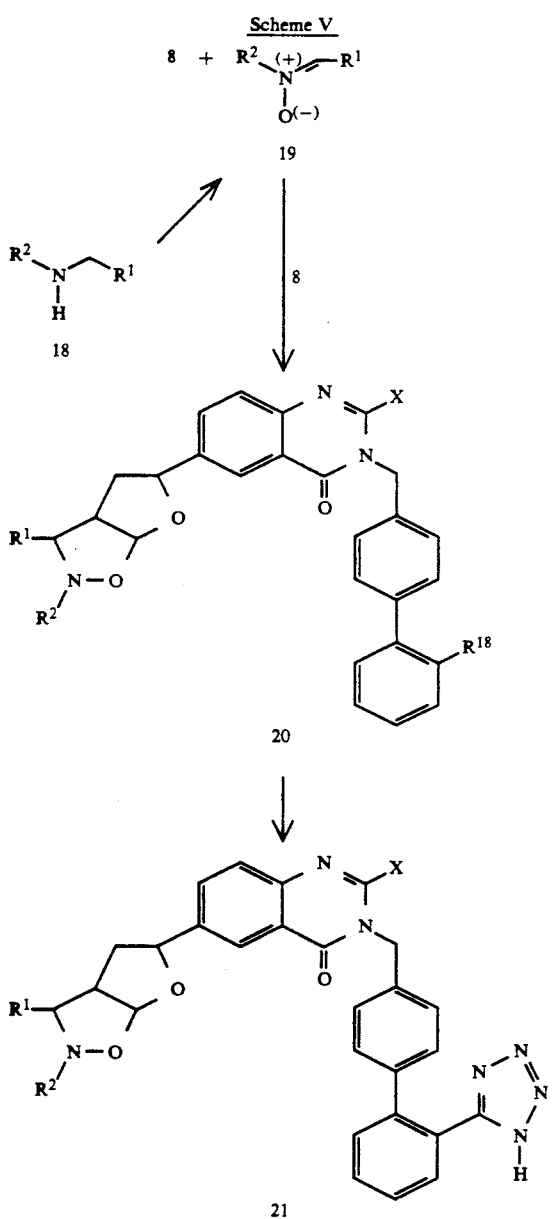

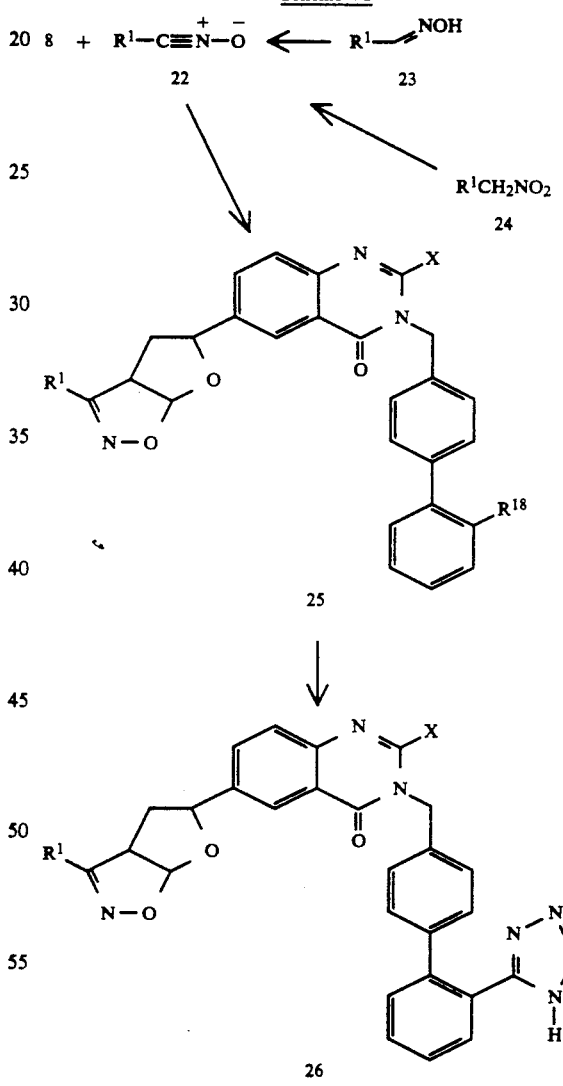

Reactions are performed in a solvent appropriate to the reagents and materials employed and suitable for the transformation being effected. It is understood by those skilled in the art of organic synthesis that the various functionalities present on the molecule must be consistent with the chemical transformations proposed. This will frequently necessitate judgement as to the order of synthetic steps, protecting groups, if required, and deprotection conditions. Substituents on the starting materials may be incompatible with some of the reaction conditions. Such restrictions to the substituents which are compatible with the reaction conditions will be apparent to one skilled in the art.

Pharmaceutically suitable salts include both the metallic (inorganic) salts and organic salts; a list of which is given in *Remington's Pharmaceutical Sciences,* 17th Edition, pg. 1418 (1985). It is well known to one skilled in the art that an appropriate salt form is chosen based on physical and chemical stability, flowability, hygroscopicity and solubility. Preferred salts of this invention for the reasons cited above include potassium, sodium, calcium, magnesium and ammonium salts.

Some of the compounds of the hereinbefore described schemes have centers of asymmetry. The compounds may, therefore, exist in at least two and often more stereoisomeric forms. The present invention encompasses all stereoisomers of the compounds whether free from other stereoisomers or admixed with other stereoisomers in any proportion and thus includes, for instance, racemic mixture of enantiomers as well as the diastereomeric mixture of isomers. The absolute configuration of any compound may be determined by conventional X-ray cyrstallography.

While the invention has been illustrated using the trityl protecting group on the tetrazole, it will be apparent to those skilled in the art that other nitrogen protecting groups may be utilized. Contemplated equivalent protecting groups include, benzyl, p-nitrobenzyl, propionitrile or any other protecting group suitable for protecting the tetrazole nitrogen. Additionally, it will be apparent to those skilled in the art that removal of the various nitrogen protecting groups, other than trityl, may require methods other than dilute acid.

The compounds of this invention and their preparation are illustrated by the following non-limiting examples.

EXAMPLE 1

2-Butyl-6-iodo-4(1H)-quinazolinone

To 20.0 g of 2-amino-5-iodobenzoic acid is added 75 ml of valeric anhydride. The mixture is heated at reflux for 18 hours and then concentrated under reduced pressure. The resulting residue is suspended in 200 ml of 30% ammonium hydroxide and 300 ml of ethyl alcohol. This mixture is heated at reflux for 18 hours and then allowed to cool to room temperature. After cooling, the precipitate is collected and crystallized from ethyl alcohol to give 3.22 g of the desired product as a solid, m.p. 258°-260° C.

EXAMPLE 2

2-Butyl-6-iodo-3-[[2'-[1-(triphenylmethyl)-1H-tetrazol-5-yl][1,1'-biphenyl]-4-yl][1,1'-biphenyl]-4-yl]methyl]-4(3H)-quinazolinone A solution of 5.00 g of 2-butyl-6-iodo-4(1H)quinazolinone, 16.98 g of 5-[4,-(bromomethyl)[1,1'biphenyl]-2-yl]-1-(triphenylmethyl)-1H-tetrazole and 18.3 ml of a 1.0M solution of lithium trimethylsilylamide in 60 ml of tetrahydrofuran is heated at reflux for 48 hours. The reaction mixture is cooled to room temperature and evaporated in vacuo to a residue which is purified by column chromatography on silica gel using 1:5 ethyl acetate-hexanes to give 6.706 g of the desired product as a solid. FAB mass spec 805 (M+H).

EXAMPLE 3

2-Butyl-6-(2,3-dihydro-2-furanyl)-3-[[2'-[1-(triphenylmethyl)-1H-tetrazol-5-yl][1,1'-biphenyl]-4-yl]methyl]-4(3H)-quinazolinone

EXAMPLE 4

2-Butyl-6-(2,5-dihydro-2-furanyl)-3-[[2'-[1-(triphenylmethyl)-1H-tetrazol-5-yl][1,1'-biphenyl]-4-yl]methyl]4(3H)-quinazolinone To a solution of 6.70 g of 2-butyl-6-iodo-3-[[2'-[1-(triphenylmethyl)-1H-tetrazol-5-yl][1,1'-biphenyl]-4-yl][1,1'-biphenyl]-4-yl]methyl-4(3H)-quinazolinone, 3.15 ml of 2,3-dihydrofuran, 2.77 g of tetrabutylammonium bromide, 0.055 g of triphenyl phosphine and 2.456 g of potassium acetate in 55 ml of N,N-dimethylformamide is added 0.047 g of palladium acetate. The reaction mixture is heated at 80° C. for 18 hours. The reaction mixture is cooled, diluted with ether then washed with water. The organic layer is chromatographed on a column of silica gel by elution with 1:3 ethyl acetate-hexanes to give 2.52 g of the 2,3-dihydro derivative, FAB mass spec 769 (M+Na), and 0.71 g of the 2,5 dihydro derivative, FAB mass spec 769 (M+Na).

EXAMPLE 5

(1α,3aα, 8aβ, 8bα)-2-Butyl-6-(octahydro-6,6-dimethylfuro[3,4-d]-pyrrolo[1,2-b]isoxazol-1-yl)-3-[[2'-[1-(triphenylmethyl)-1H-tetrazol-5-yl]-[1,1'-biphenyl]-4-yl]methyl]-4(3H)-quinazolinone

EXAMPLE 6

(3α, 3aα, 8aβ, 8bα)-2-Butyl-6-(6,6-dimethyloctahydrofuro[3,4-d][1,2-b]isoxazol-3-yl)-3-[[2'-[1-(triphenylmethyl)-1H-tetrazol-5-yl][1,1'biphenyl]-4-yl]methyl]-4-(3H)-quinazolinone A mixture of 0.300 g of 2-butyl-6-(2,3-dihydro-2-furanyl)-3-[[2'-[1-(triphenylmethyl)-1H-tetrazol-5-yl][1,1'-biphenyl]-4-yl]methyl]-4(3H)-quinazolinone and 0.137 g of 5,5-dimethyl-1-pyrroline N-oxide in 6 ml of toluene is heated at reflux for 12 hours, cooled and evaporated to a residue in vacuo. The residue is purified by column chromatography on silica gel using 1:1 ethyl acetate-hexanes to give 0.116 g of the first desired product as a solid, FAB mass spec 882 (M+Na), and 0.057 g of the second desired product as a solid, FAB mass spec 882 (M+Na).

EXAMPLE 7

(1α, 3aα, 8aβ, 8bα)-2-Butyl-6-(octahydro-6,6-dimethylfuro[3,4-d]pyrrolo[1,2-b]isoxazol-1-yl)-3-[[2'-(1H-tetrazol-5-yl)[1,1'-biphenyl]-4-yl]methyl]-4(3H)-quinazolinone A mixture of 0.109 g of (1α,3aα, 8aβ, 8bα)-2-butyl-6-(octahdyro-6,6-dimethylfuro[3,4-d]pyrrolo[1,2-b]isoxazol-1-yl)-3-[[2'-[1-(triphenylmethyl)-1H-tetrazol-5-yl]-[1,1'-biphenyl]-4-yl]methyl]-4(3H)-quinazolinone in 5.0 ml of methanol and 1.0 ml of tetrahydrofuran is heated at reflux for 16 hours. The volatiles are evaporated in vacuo to a residue which is purified by column chromatography on silica gel by elution with 99:1 chloroform-methanol to give 0.053 g of the desired product as a solid, FAB mass spec 618 (M+H).

EXAMPLE 8

(3α, 3aα, 8aβ, 8bα)'-2-Butyl-6-(6,6-dimethylocta hydrofuro[3,4-d][1,2-b]isoxazol-3-yl)-3[[2'-(1H-tetrazol-5-yl)[1,1'biphenyl]-4yl]methyl]-4(3H) quinazolinone A mixture of 0.048 g of (3α, 3aα, 8aβ, 8bα)-2-butyl-6-(6,6-dimethyloctahydrofuro[3,4-d][1,2-b]isoxazol-3-yl)-3-[[2'-[1-(triphenylmethyl)-1H-tetrazol-5-yl][1,1'-biphenyl]-4-yl]methyl]-4-(3H)-quinazolinone in 1.0 ml of tetrahydrofuran and 5.0 ml of methanol is heated at reflux for 18 hours. The volatiles are evaporated in vacuo to a residue which is purified by column chromatography on silica gel by elution with 99:1 chloroform-methanol to give 0.025 g of the desired product as a solid. FAB mass spec 618 (M+H).

EXAMPLE 9

(3α, 3aβ, 5β, 6aβ)-2-Butyl-6-(hexahydro-2,3-diphenylfuro[3,2-d]isoxazol-5-yl)-3-[[2'-[1-(triphenyl methyl)-1H-tetrazol-5-yl][1,1'-biphenyl]-4-yl]methyl]-4(3H)-quinazolinone A mixture of 2-butyl-6-(2,3-dihydro-2-furanyl)-3-[[2'-[1-(triphenylmethyl)-1H-tetrazol-5-yl][1,1'-biphenyl]-4-yl]methyl]-4(3H)-quinazolinone, 0.132 g of N-α-diphenylnitrone and 5 ml of toluene is heated at reflux for 18 hours. The volatiles are evaporated in vacuo to a residue which is purified by column chromatography on silica gel using 1:3 ethyl acetatehexanes to give 0.108 g of the desired product as a solid. FAB mass spec 966 (M+Na).

EXAMPLE 10

(3α, 3aβ, 5β, 6aβ)-2-Butyl-6-(hexahydro-2,3-diphenylfuro[3,2-d]isoxazol-5-yl)-3-[[2'-(1H-tetrazol-5-yl)[1,1'-biphenyl]-4-yl]methyl]-4(3H)-quinazolinone A mixture of 0.099 g of (α, 3aβ, 5β, 6aβ)-2-butyl-6-(hexahydro-2,3-diphenylfuro[3,2-d]isoxazol-5-yl)-3-[[2'-[1-(triphenylmethyl)-1H-tetrazol-5-yl][1,1'-biphenyl]-4-yl]methyl]-4(3H)-quinazolinone in 5.0 ml of methanol and 1.0 ml of tetrahydrofuran is heated at reflux for 18 hours then evaporated in vacuo to a residue which is purified by column chromatography on silica gel using 99:1 chloroform-methanol to give 0.053 g of the desired product as a solid.

EXAMPLE 11

(3aα, 5α, 6aα)-2-Butyl-6-[3a, 4, 5, 6a-tetra hydro-3-(4-methylphenyl)furo[3,2-d]isoxazol-5-yl]-3 [[2'-[1-(triphenylmethyl)-1H-tetrazol-5-yl][1,1-bi phenyl]-4-yl]methyl]-4(3H)-quinazolinone To a suspension of 0.045 g of N-chlorosuccinimide in 2.0 ul of pyridine and 1.0 ml of chloroform is added p-tolualdehyde oxime. The reaction mixture is stirred at room temperature for 30 minutes then 0.250 g of 2-butyl-6-(2,3-dihydro-2-furanyl)-3-[[2'-[1-(triphenylmethyl)-1H-tetrazol-5-yl][1,1'-biphenyl]-4-yl]methyl]-4(3H)-quinazolinone is added. While stirring 49 ul of triethylamine is added dropwise over 15 minutes. The reaction mixture is stirred at room temperature for 18 hours. The volatiles are evaporated in vacuo and the residue purified by column chromatography on silica gel with 1:1 ethyl acetate-hexanes to give 0.155 g of the desired product as a solid. FAB mass spec 902 (M+Na).

EXAMPLE 12

(3aα, 5α, 6aα)-2-Butyl-6-(3aα, 4, 5, 6a-tetra-hydro-3-(4-methylphenyl)furo[3,2-d1isoxazol-5-yl)-3-[[2'-(1-tetrazol-5-yl)[1,1'-biphenyl]-4-yl]-methyl]-4(3H)-quinazolinone A mixture of 0.115 g of (3aα, 5α, 6aβ)-2-butyl-6-[3a, 4, 5, 6a-tetrahydro-3-(4-methylphenyl)furo[3,2-d]isoxazol-5-yl]-3[[2'-[1-(triphenylmethyl)-1H-tetrazol-5-yl][1,1'biphenyl]-4-yl]methyl]-4(3H)-quinazolinone in 5.0 ml of methanol and 1.0 ml of tetrahydrofuran is heated at reflux for 18 hours. The reaction mixture is evaporated in vacuo to a residue which is purified by column chromatography on silica gel using 99:1 chloroform-methanol to give 0.053 g of the desired product as a solid. FAB mass spec 638 (M+H).

EXAMPLE 13

(2α, 4aα, 4bβ, 8aα)-2-Butyl-6-(6,6-dimethyloctahydrofuro[3,2-d]pyrrolo[1,2-b]isoxazol-2-yl)-3-[[2'-[1-(triphenylmethyl)-1H-tetrazol-5-yl][1,1'-biphenyl]-4-yl]methyl-4-(3H)-quinazolinone A mixture of 0.114 g of 5,5-dimethyl-1-pyrroline N-oxide and 0.250 g of 2-butyl-6-(2,3-dihydro-2-furanyl)-3-[[2'-[1-(triphenylmethyl)-1H-tetrazol-5-yl]-[[1,1'-biphenyl]-4-yl]methyl]-4(3H)-quinazolinone in 5.0 ml of toluene is heated at reflux for 10 hours, cooled and evaporated in vacuo to a residue. The residue is purified by high pressure liquid chromatography using 1:2 ethyl acetate-hexanes to give 0.068 g of the desired product as a solid. FAB mass spec 860 (M+H).

EXAMPLE 14

(2α, 3aα, 3bβ, 8aα)-2-Butyl-6-(6,6-dimethyloctahydrofuro[3,2-d]pyrrolo[[1,2-d]-isoxazol-2-yl)-3-[[2'-(1H-tetrazol-5-yl)[1,1'-biphenyl]-4-yl]methyl]-4(3H)-quinazolinone A mixture of 0.063 g of (2α, 4aα, 4bβ, 8aα)-2-butyl-6-(6,6-dimethyl-octahydrofuro[3,2-d]pyrrolo[1,2-b]isoxazol-2-yl)-3-[[2'-[1-(triphenylmethyl)-1H-tetrazol-5-yl]-[1,1'-biphenyl]-4-yl]methyl-4-quinazolinone, 5.0 ml of methanol and 1.0 ml of tetrahydrofuran is heated at reflux for 18 hours then evaporated to a residue which is purified by column chromatography on silica gel using 99:1 chloroform-methanol to give 0.042 g, of the desired product as a solid. FAB mass spec 618 (M+H).

Angiotensin II Antagonists In Vitro Tests Materials and Methods

Beef adrenals are obtained from a local slaughter house (Maxwell-Cohen).

[$^{125}$I](Sar$^1$,Ile$^8$)AngII, S.A. 2200 Ci/mmole, is purchased from Dupont (NEN ®, Boston, Mass.). All unlabeled AngII analogs, Dimethylsulfoxide (DMSO), nucleotides, bovine serum albumin (BSA) are purchased from Sigma Chemical Co., St. Louis, Mo. U.S.A.

Preparation of Membranes

Approximately sixteen (16) to twenty (20) beef adrenal glands are processed as follows: fresh adrenal glands received on crushed ice are cleaned of fatty tissues and the tough membranes encapsulating the glands are removed and discarded. The brownish tissue forming the adrenal cortex is scraped off and finely minced with scissors before homogenization. Care is taken to avoid contamination with medullary tissue during dissection. The scraped cortices are suspended in twenty volumes of an ice-cold buffer medium consisting of 10 mM Tris.HCl (pH 7.4 at 22° C.) and containing 1.0 mM EDTA and 0.2M sucrose. Unless otherwise indicated, all subsequent operations are done at 4° C. The tissue is homogenized in a glass homogenizer with a motor-driven teflon pestle with a clearance of 1.0 mm. The homogenate is centrifuged first at low speed ($3,000 \times g$) for 10 min. The resulting pellet is discarded and the supernatant fluid recentrifuged at $10,000 \times g$ for 15 minutes to give a $P_2$ pellet. This $P_2$ pellet is discarded and the liquid phase is carefully decanted off in clean centrifuge tubes and recentrifuged at high speed ($100,000 \times g$) for 60 min. The translucent final pellet is harvested and combined in a small volume (20–50.0 ml) of 50.0 mM Tris.HCl buffer, pH 7.2. A 100 ul aliquot is withdrawn and the protein content of the preparation is determined by the Lowry's method (Lowry, O. H., Rosebrough, N. F., Farr, A. L. and Randall, R. J., Protein measurement with Folin phenol reagent. J. Biol. Chem., 48, 265–275, 1951). The pelleted membrane is reconstituted in 50.0 mM Tris.HCl buffer containing 0.1 mM of phenylmethylsulfonyl fluoride (PMSF) to give approximately a protein concentration of 2.5 mg per ml of tissue suspension. The membrane preparation is finally aliquoted in 1.0 ml volumes and stored at $-70°$ C. until use in the binding assays.

Receptor Binding Assay

Binding of[$^{125}$I](Sar$^1$, Ile$^8$)AngII

The binding of [$^{125}$I](Sar$^1$.Ile$^8$)AngII to microsomal membranes is initiated by the addition of reconstituted membranes (1:10 vols.) in freshly made 50.0 mM Tris.HCl buffer, pH 7.4 containing 0.25% heat inactivated bovine serum albumin (BSA): 80 ul membrane protein (10 to 20 ug/assay) to wells already containing 100 ul of incubation buffer (as described above) and 20 ul [$^{125}$I](Sar$^1$,Ile$^8$)AmgII (Specific Activity, 2200 Ci/m-mole) Non-specific binding is measured in the presence of 1.0 uM unlabeled (Sar$^1$,Ile$^8$)AngII, added in 20 ul volume. Specific binding for [$^{125}$I](Sar$^1$,Ile$^8$) AngII is greater than 90%. In competition studies, experimental compounds are diluted in dimethylsulfoxide (DMSO) and added in 20 ul to wells before the introduction of tissue membranes. This concentration of DMSO is found to have no negative effects on the binding of [125I] (Sar$^1$,Ile$^8$) AngII to the membranes. Assays are performed in triplicate. The wells are left undisturbed for 60 min. at room temperature. Following incubation, all wells are harvested at once with a Brandel ® Harvester especially designed for a 96 well plate (Brandel ® Biomedical Research & Development Labs. Inc., Gaithersburg, Md., U.S.A.). The filter discs are washed with $10 \times 1.0$ ml of cold 0.9% NaCl to remove unbound ligand. Presoaking the filter sheet in 0.1% polyethyleneimine in normal saline (PEI/Saline) greatly reduces the radioactivity retained by the filter blanks. This method is routinely used. The filters are removed from the filter grid and counted in a Parkard ® Cobra Gamma Counder for 1 min. (Packard Instrument Co., Downers Grove, Ill., U.S.A.). The binding data are analyzed by the non-linear interactive "LUNDON-1" program (LUNDON SOFTWARE Inc., Cleveland, Ohio U.S.A.). Compounds that displace 50% of the labelled angiotensin II at the screening dose of 50 μM are considered active compounds and are then evaluated in concentration-response experiments to determine their $IC_{50}$ values. The results are shown in Table I.

TABLE I

| Ex. No. | R$_6$ | X | Angiotensin II Receptor Binding IC$_{50}$ (M) |
|---|---|---|---|
| 7 | [structure] | $-(CH_2)_3CH_3$ | $50.0 \times 10^{-9}$ |
| 8 | [structure] | $-(CH_2)_3CH_3$ | $37.0 \times 10^{-9}$ |
| 10 | [structure] | $-(CH_2)_3CH_3$ | $76.0 \times 10^{-9}$ |

TABLE I-continued

| Ex. No. | R$_6$ | X | Angiotensin II Receptor Binding IC$_{50}$ (M) |
|---|---|---|---|
| 12 | [structure: 4-methylphenyl group attached to nitrone-containing ring with stereochemistry] | —(CH$_2$)$_3$CH$_3$ | 10.0 × 10$^{-8}$ |
| 14 | [structure: bicyclic isoxazolidine with gem-dimethyl group] | —(CH$_2$)$_3$CH$_3$ | 31.9 × 10$^{-9}$ |

As can be seen from Table I, the compounds demonstrate excellent Angiotensin II Receptor Binding activity.

The enzyme renin acts on a blood plasma $\alpha_2$-globulin, angiotensinogen, to produce angiotensin I, which is then converted by angiotensin converting enzyme to AII. The substance AII is a powerful vasopressor agent which is implicated as a causative agent for producing high blood pressure in mammals. Therefore, compounds which inhibit the action of the hormone angiotensin II (AII) are useful in alleviating angiotensin induced hypertension.

The compounds of this invention inhibit the action of AII. By administering a compound of this invention to a rat, and then challenging with angiotensin II, a blockage of the vasopressor response is realized. The results of this test on representative compounds of this invention are shown in Table II.

AII Challenge

Conscious Male Okamoto-Aoki SHR, 16–20 weeks old, weighing approximately 330 g are purchased from Charles River Labs (Wilmington, Mass.). Conscious rats are restrained in a supine position with elastic tape. The area at the base of the tail is locally anesthetized by subcutaneous infiltration with 2% procaine. The ventral caudal artery and vein are isolated, and a cannula made of polyethylene (PE) 10–20 tubing (fused together by heat) is passed into the lower abdominal aorta and vena cava, respectively. The cannula is secured, heparinized (1,000 I.U./ml), sealed and the wound is closed. The animals are placed in plastic restraining cages in an upright position. The cannula is attached to a Statham P23Db pressure transducer, and pulsatile blood pressure is recorded to 10–15 minutes with a Gould Brush recorder. (Chan et al., (Drug Development Res., 18:75–94, 1989).

Angiotensin II (human sequence, Sigma Chem. Co., St. Louis, Mo.) of 0.05 and 0.1 ug/kg i.v. is injected into all rats (predosing response). Then a test compound, vehicle or a known angiotensin II antagonist is administered i.v., i.p. or orally to each set of rats. The two doses of angiotensin II are given to each rat again at 30, 60, 90, 120, 180, 240 and 300 minutes post dosing the compound or vehicle. The vasopressor response of angiotensin II is measured for the increase in systolic blood pressure in mmHg. The percentage of antagonism or blockade of the vasopressor response of angiotensin II by a compound is calculated using the vasopressor response (increase in systolic blood pressure) of angiotensin II of each rat predosing the compound as 100%. A compound is considered active if at 30 mg/kg i.v. it antagonized at least 50% of the response.

TABLE II

| | | ANGIOTENSIN II (AII) VASOPRESSOR RESPONSE | | | | | | |
|---|---|---|---|---|---|---|---|---|
| | Dose (mg/kg) | AII Dose mcg/kg IV | Min Post Dose | Control Before AII | Response After AII | Change | Average Change | % Inhibition |
| CONTROL | | 0.05 | 0 | 240 | 285 | 45 | 47.5 | |
| | | | | 225 | 275 | 50 | | |
| | | 0.1 | | 240 | 295 | 55 | 52.5 | |
| | | | | 230 | 280 | 50 | | |
| Ex. No. 7 | 3 I.V. | 0.05 | 30 | 245 | 245 | 0 | 4.5 | 91 |
| | | | | 214 | 223 | 9 | | |
| | | 0.1 | | 255 | 260 | 5 | 5 | 90 |
| | | | | 220 | 225 | 5 | | |
| | | 0.05 | 60 | 240 | 255 | 15 | 7.5 | 84 |
| | | | | 225 | 225 | 0 | | |
| | | 0.1 | | 250 | 255 | 5 | 7.5 | 86 |
| | | | | 215 | 225 | 10 | | |
| | | 0.05 | 90 | 235 | 240 | 5 | 5 | 89 |
| | | | | 235 | 240 | 5 | | |
| | | 0.1 | | 235 | 238 | 3 | 9 | 83 |
| | | | | 225 | 240 | 15 | | |
| | | 0.05 | 120 | 225 | 235 | 10 | 7.5 | 84 |

TABLE II-continued

| | Dose (mg/kg) | AII Dose mcg/kg IV | Min Post Dose | Control Before AII | Response After AII | Change | Average Change | % Inhibition |
|---|---|---|---|---|---|---|---|---|
| | | | | 220 | 225 | 5 | | |
| | | 0.1 | | 235 | 240 | 5 | 7.5 | 86 |
| | | | | 215 | 225 | 10 | | |
| | | 0.05 | 180 | 225 | 235 | 10 | 10 | 79 |
| | | | | 215 | 225 | 10 | | |
| | | 0.1 | | 235 | 245 | 10 | 14.5 | 72 |
| | | | | 205 | 224 | 19 | | |
| | | 0.05 | 240 | 225 | 235 | 10 | 17.5 | 63 |
| | | | | 215 | 240 | 25 | | |
| | | 0.1 | | 235 | 245 | 10 | 10 | 81 |
| | | | | 225 | 235 | 10 | | |
| | | 0.05 | 300 | 235 | 242 | 7 | 12.5 | 74 |
| | | | | 210 | 228 | 18 | | |
| | | 0.1 | | 230 | 250 | 20 | 22.5 | 57 |
| | | | | 215 | 240 | 25 | | |

SPONTANEOUSLY HYPERTENSIVE RATS n = 2 Body weight(s): 380, 355 grams

ANGIOTENSIN II (AII) VASOPRESSOR RESPONSE

| | Dose (mg/kg) | AII Dose mcg/kg IV | Min Post Dose | Control Before AII | Response After AII | Change | Average Change | % Inhibition |
|---|---|---|---|---|---|---|---|---|
| CONTROL | | 0.05 | 0 | 230 | 265 | 35 | 37.5 | |
| | | | | 205 | 245 | 40 | | |
| | | 0.1 | | 220 | 270 | 50 | 42.5 | |
| | | | | 210 | 245 | 35 | | |
| Ex. No. 7 | 3 p.o. | 0.05 | 30 | 215 | 248 | 33 | 29 | 23 |
| | | | | 205 | 230 | 25 | | |
| | | 0.1 | | 215 | 260 | 45 | 40 | 6 |
| | | | | 200 | 235 | 35 | | |
| | | 0.05 | 60 | 230 | 255 | 25 | 27.5 | 27 |
| | | | | 195 | 225 | 30 | | |
| | | 0.1 | | 215 | 255 | 40 | 40 | 6 |
| | | | | 195 | 235 | 40 | | |
| | | 0.05 | 90 | 210 | 245 | 35 | 26 | 31 |
| | | | | 193 | 210 | 17 | | |
| | | 0.1 | | 215 | 260 | 45 | 35 | 18 |
| | | | | 195 | 220 | 25 | | |
| | | 0.05 | 120 | 210 | 245 | 35 | 27.5 | 27 |
| | | | | 195 | 215 | 20 | | |
| | | 0.1 | | 205 | 240 | 35 | 32.5 | 24 |
| | | | | 190 | 220 | 30 | | |
| | | 0.05 | 180 | 210 | 255 | 45 | 37.5 | 0 |
| | | | | 190 | 220 | 30 | | |
| | | 0.1 | | 215 | 260 | 45 | 37.5 | 12 |
| | | | | 180 | 210 | 30 | | |
| | | 0.05 | 240 | 210 | 260 | 50 | 37.5 | 0 |
| CONTROL | | | | 190 | 215 | 25 | | |
| | | 0.1 | | 213 | 265 | 52 | 38.5 | 9 |
| | | | | 185 | 210 | 25 | | |

SPONTANEOUSLY HYPERTENSIVE RATS n = 2 Body weight(s): 325, 330 grams

ANGIOTENSIN II (AII) VASOPRESSOR RESPONSE

| | Dose (mg/kg) | AII Dose mcg/kg IV | Min Post Dose | Control Before AII | Response After AII | Change | Average Change | % Inhibition |
|---|---|---|---|---|---|---|---|---|
| CONTROL | | 0.05 | 0 | 220 | 280 | 60 | 55 | |
| | | 0.1 | | 215 | 265 | 50 | | |
| | | 0.1 | | 205 | 290 | 85 | 71.5 | |
| | | | | 210 | 268 | 58 | | |
| Ex. No. 10 | 1 i.v. | 0.05 | 30 | 248 | 290 | 42 | 33.5 | 39 |
| | | | | 230 | 255 | 25 | | |
| | | 0.1 | | 250 | 295 | 45 | 42.5 | 41 |
| | | | | 220 | 260 | 40 | | |
| | 29 i.v. | 0.05 | 60 | 265 | 270 | 5 | 10 | 82 |
| | | | | 235 | 250 | 15 | | |
| | | 0.1 | | 265 | 270 | 5 | 10 | 86 |
| | | | | 230 | 245 | 15 | | |
| | | 0.05 | 90 | 235 | 250 | 15 | 10 | 82 |
| | | | | 230 | 235 | 5 | | |
| | | 0.1 | | 230 | 250 | 20 | 20 | 72 |
| | | | | 235 | 255 | 20 | | |
| | | 0.05 | 120 | 210 | 225 | 15 | 12.5 | 77 |
| | | | | 240 | 250 | 10 | | |

-continued

| | Dose (mg/kg) | AII Dose mcg/kg IV | Min Post Dose | Control Before AII | Response After AII | Change | Average Change | % Inhibition |
|---|---|---|---|---|---|---|---|---|
| | | 0.1 | | 200 | 230 | 30 | 25 | 65 |
| | | | | 215 | 235 | 20 | | |
| | | 0.05 | 180 | 215 | 235 | 20 | 15 | 73 |
| | | | | 220 | 230 | 10 | | |
| | | 0.1 | | 210 | 225 | 15 | 15 | 79 |
| | | | | 220 | 235 | 15 | | |
| | | 0.05 | 240 | 220 | 235 | 15 | 10 | 82 |
| | | | | 215 | 220 | 5 | | |
| | | 0.1 | | 215 | 235 | 20 | 15 | 79 |
| | | | | 215 | 225 | 10 | | |
| | | 0.05 | 300 | 210 | 220 | 10 | 15 | 73 |
| | | | | 200 | 220 | 20 | | |
| | | 0.1 | | 210 | 230 | 20 | 15 | 79 |
| | | | | 210 | 220 | 10 | | |

SPONTANEOUSLY HYPERTENSIVE RATS n = 2 Body weight(s): 360, 335 grams

| | Dose (mg/kg) | AII Dose mcg/kg IV | Min Post Dose | Control Before AII | Response After AII | Change | Average Change | % Inhibition |
|---|---|---|---|---|---|---|---|---|
| CONTROL | | 0.05 | 0 | 210 | 255 | 45 | 37.5 | |
| | | | | 255 | 285 | 30 | | |
| | | 0.1 | | 210 | 260 | 50 | 39 | |
| | | | | 260 | 288 | 28 | | |
| Ex. No. 12 | 3 i.v. | 0.05 | 30 | 220 | 233 | 13 | 16.5 | 56 |
| | | | | 255 | 275 | 20 | | |
| | | 0.1 | | 218 | 245 | 27 | 18.5 | 53 |
| | | | | 250 | 260 | 10 | | |
| | | 0.05 | 60 | 215 | 235 | 20 | 17.5 | 53 |
| | | | | 245 | 260 | 15 | | |
| | | 0.1 | | 220 | 245 | 25 | 22.5 | 42 |
| | | | | 240 | 260 | 20 | | |
| | | 0.05 | 90 | 225 | 240 | 15 | 15 | 60 |
| | | | | 235 | 250 | 15 | | |
| | | 0.1 | | 220 | 250 | 30 | 27.5 | 29 |
| | | | | 230 | 255 | 25 | | |
| | | 0.05 | 120 | 207 | 233 | 26 | 20.5 | 45 |
| | | | | 225 | 240 | 15 | | |
| | | 0.1 | | 205 | 240 | 35 | 30 | 23 |
| | | | | 225 | 250 | 25 | | |
| | | 0.05 | 180 | 195 | 225 | 30 | 25 | 33 |
| | | | | 225 | 245 | 20 | | |
| | | 0.1 | | 205 | 225 | 20 | 22.5 | 42 |
| | | | | 225 | 250 | 25 | | |
| | | 0.05 | 240 | 220 | 240 | 20 | 17.5 | 53 |
| | | | | 230 | 245 | 15 | | |
| | | 0.1 | | 220 | 260 | 40 | 35 | 10 |
| | | | | 225 | 255 | 30 | | |
| | | 0.05 | 300 | 220 | 245 | 25 | 19.5 | 48 |
| | | | | 230 | 244 | 14 | | |
| | | 0.1 | | 220 | 255 | 35 | 35 | 10 |
| | | | | 225 | 260 | 35 | | |

SPONTANEOUSLY HYPERTENSIVE RATS n = 2 Body weight(s): 360, 340 grams

| | Dose (mg/kg) | AII Dose mcg/kg IV | Min Post Dose | Control Before AII | Response After AII | Change | Average Change | % Inhibition |
|---|---|---|---|---|---|---|---|---|
| CONTROL | | 0.05 | 0 | 215 | 250 | 35 | 35 | |
| | | | | 245 | 280 | 35 | | |
| | | 0.1 | | 225 | 255 | 30 | 40 | |
| | | | | 240 | 290 | 50 | | |
| Ex. No. 14 | 3 i.v. | 0.05 | 30 | 225 | 225 | 0 | 7.5 | 79 |
| | | | | 240 | 250 | 15 | | |
| | | 0.1 | | 230 | 240 | 10 | 17.5 | 56 |
| | | | | 245 | 270 | 25 | | |
| | | 0.05 | 60 | 225 | 235 | 10 | 12.5 | 64 |
| | | | | 240 | 255 | 15 | | |
| | | 0.1 | | 215 | 235 | 20 | 17.5 | 56 |
| | | | | 245 | 260 | 15 | | |
| | | 0.05 | 90 | 225 | 235 | 10 | 9 | 74 |
| | | | | 237 | 245 | 8 | | |
| | | 0.1 | | 220 | 235 | 15 | 16 | 60 |

-continued

| Dose (mg/kg) | AII Dose mcg/kg IV | Min Post Dose | Control Before AII | Response After AII | Change | Average Change | % Inhibition |
|---|---|---|---|---|---|---|---|
|  |  |  | 240 | 257 | 17 |  |  |
|  | 0.05 | 120 | 210 | 215 | 5 | 8.5 | 76 |
|  |  |  | 230 | 242 | 12 |  |  |
|  | 0.1 |  | 215 | 230 | 15 | 15 | 63 |
|  |  |  | 230 | 245 | 15 |  |  |
|  | 0.05 | 180 | 215 | 225 | 10 | 8.5 | 76 |
|  |  |  | 230 | 237 | 7 |  |  |
|  | 0.1 |  | 215 | 225 | 10 | 12.5 | 69 |
|  |  |  | 230 | 245 | 15 |  |  |
|  | 0.05 | 240 | 205 | 215 | 10 | 10 | 71 |
|  |  |  | 230 | 240 | 10 |  |  |
|  | 0.1 |  | 215 | 230 | 15 | 17.5 | 56 |
|  |  |  | 225 | 245 | 20 |  |  |
|  | 0.05 | 300 | 220 | 228 | 8 | 9 | 74 |
|  |  |  | 235 | 245 | 10 |  |  |
|  | 0.1 |  | 215 | 233 | 18 | 21.5 | 46 |
|  |  |  | 235 | 260 | 25 |  |  |

SPONTANEOUSLY HYPERTENSIVE RATS n = 2 Body weight(s): 385, 365 grams

When the compounds are employed for the above utility, they may be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspension containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 500 mg/kg of animal body weight, preferably given in divided doses two to four times a day, or in sustained release form. For most large mammals the total daily dosage is from about 1 to 100 mg, preferably from about 2 to 80 mg. Dosage forms suitable for internal use comprise from about 0.5 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

We claim:

1. A quinazolinone compound having the formula:

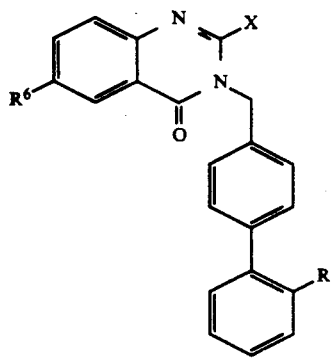

wherein:
R is

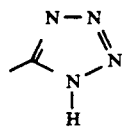

X is a straight chain alkyl of 3 or 4 carbon atoms;
R⁶ is

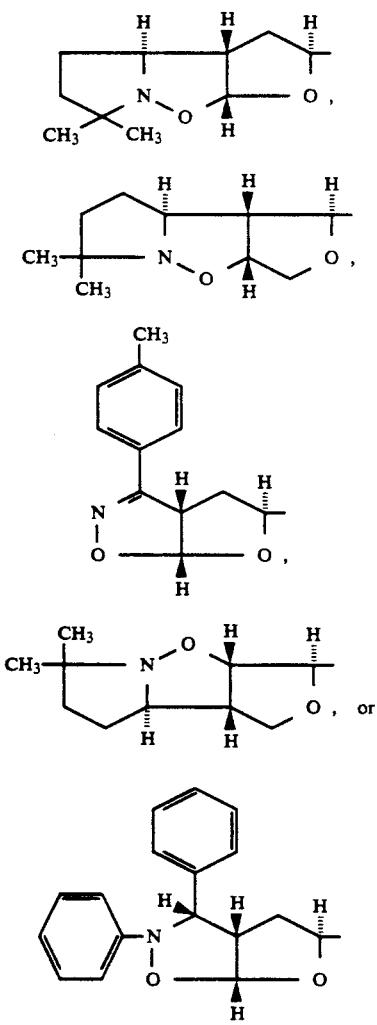

or the pharmaceutically acceptable salts thereof.

2. The salts according to claim 1 wherein said salts are selected from potassium, sodium, calcium, magnesium or ammonium.

3. A method of treating congestive heart failure in a mammal comprising administering a compound of claim 1 to said mammal in an amount effective to treat congestive heart failure.

4. A quinazolinone compound having the formula:

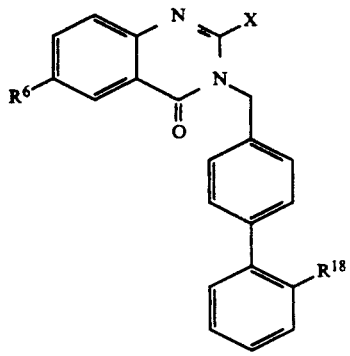

wherein:
R¹⁸ is

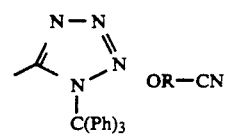

X is a straight chain alkyl of 3 or 4 carbon atoms;
R⁶ is

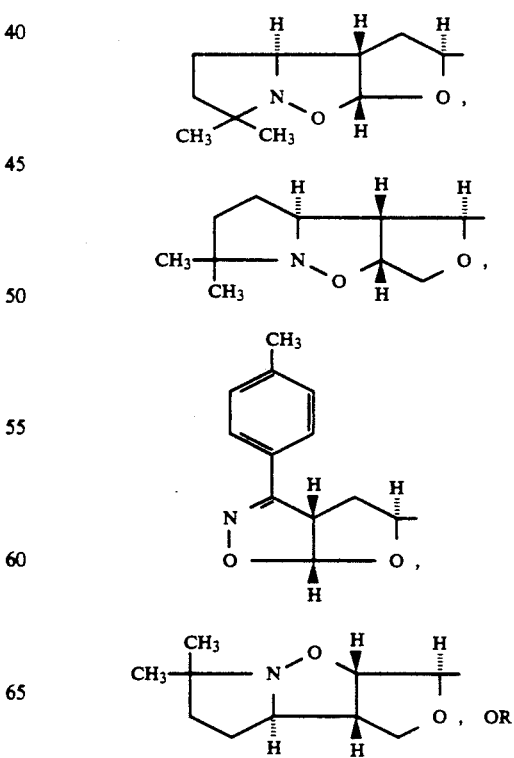

-continued

5. A method antagonizing the effects of Angiotensin II in a mammal comprising administering a compound of claim 1 to said mammal in an amount effective to treat the effects of Angiotensin II.

6. The compound according to claim 4 wherein $R^{18}$ is

7. The compound according to claim 4 wherein $R^{18}$ is —CN.

8. The compound according to claim 1 (1α,3aα, 8aβ, 8bα)-2-butyl-6-(octahydro-6,6-dimethylfuro[3,4-d]pyrrolo[1,2-b]isoxazol-1-yl)-3-[[2'-(1H-tetrazol-5-yl)[1,1'-biphenyl]-4-yl]methyl]-4(3H)-quinazolinone.

9. The compound according to claim 1, (3α, 3aα, 8aβ, 8bα)'-2-butyl-(6,6-dimethyloctahydrofuro[3,4-d][1,2-b]isoxazol-3-yl)-3[[2'-(1H-tetrazol-5-yl)[1,1-biphenyl]-4-yl]methyl]-4(3H)-quinazolinone.

10. The compound according to claim 1, (3α, 3aβ, 5β, 6aβ)-2-butyl-6-(hexahydro-2,3-diphenylfuro[3,2-d]isoxazol-5-yl)-3-[[2'-(1H-tetrazol-5-yl)[1,1-biphenyl]-4-yl]methyl]-4(3H)-quinazolinone.

11. The compound according to claim 1, (3aα, 5α, 6aα)-2-butyl-6-(3a, 4, 5, 6a-tetrahydro-3-(4-methylphenyl)furo[3,2-d]isoxazol-5-yl)-3-[[2'-(1-tetrazol-5-yl)[1,1'-biphenyl]-4-yl]-methyl]-4(3H)-quinazolinone.

12. The compound according to claim 1, (2α, 3aα, 3bβ, 8aα)-2-butyl-6-(6,6-dimethyloctahydrofuro[3,2-d]pyrrolo[[1,2-d]-isoxazol-2-yl)-3-[[2'-(1H-tetrazol-5-yl)[1,1'-biphenyl]-4-yl]methyl]-4(3H)-quinazolinone.

13. The compound according to claim 4, (1α, 3aα, 8aβ, 8bα)-2-butyl-6-(octahydro-6,6-dimethylfuro[3,4-d]-pyrrolo[1,2-b]isoxazol-1-yl)-3-[[2'-[1-(triphenylmethyl)-1H-tetrazol-5-yl]-[1,1'-biphenyl]-4-yl]methyl]-4(3H)-quinazolinone.

14. The compound according to claim 4, (3α, 3aα, 8aβ, 8bα)-2-butyl-6-(6,6-dimethyloctahydrofuro[3,4-d][1,2-b]isoxazol-3-yl)-3-[[2'-[1-(triphenylmethyl)-1H-tetrazol-5-yl][1,1-biphenyl]-4-yl]methyl]-4-(3H)-quinazolinone.

15. The compound according to claim 4, (α, 3aβ, 5β, 6aβ)-2-butyl-6-(hexahydro-2,3-diphenylfuro[3,2-d]isoxazol-5-yl)-3-[[2'-[1-(triphenylmethyl)-1H-tetrazol-5-yl][1,1'-biphenyl]-4-yl]methyl]-4(3H)-quinazolinone.

16. The compound according to claim 4, (3aα, 5α, 6aα)-2-butyl-6-[3a, 4, 5, 6a-tetrahydro-3-(4-methylphenyl)furo[3,2-d]isoxazol-5-yl]-3-[[2'-[1-(triphenylmethyl)-1H-tetrazol-5-yl][1,1'biphenyl]-4-yl]methyl]-4(3H)-quinazolinone.

17. The compound according to claim 4, (2α, 4aα, 4bβ, 8aα)-2-butyl-6-(6,6-dimethyloctahydrofuro[3,2-d]pyrrolo[1,2-b]isoxazol-2-yl)-3-[[2'-[1-(triphenylmethyl)-1H-tetrazol-5-yl]-[1,1'-biphenyl]-4-yl]methyl-4-quinazolinone.

18. The compound according to claim 4, 2-butyl-6-(2,3-dihydro-2-furanyl)-3-[[2'-[1-(triphenylmethyl)-1H-tetrazol-5-yl][1,1'-biphenyl]-4-yl]methyl]-4(3H)-quinazolinone.

19. The compound according to claim 4, 2-butyl-6-(2,5-dihydro-2-furanyl)-3-[[2'-[1-(triphenylmethyl)-1H-tetrazol-5-yl][1,1'-biphenyl]-4-yl]methyl]-4(3H)-quinazolinone.

20. A pharmaceutical composition useful for treating angiotensin induced hypertension or congestive heart failure in a mammal comprising a suitable pharmaceutical carrier and an effective amount of a compound of claim 1.

21. A method of treating angiotensin induced hypertension in a mammal comprising administering a compound of claim 1 to said mammal an amount effective to lower angiotensin induced hypertension.

* * * * *